(12) United States Patent
Govari et al.

(10) Patent No.: US 7,684,850 B2
(45) Date of Patent: Mar. 23, 2010

(54) REFERENCE CATHETER FOR IMPEDANCE CALIBRATION

(75) Inventors: Assaf Govari, Haifa (IL); Andres Claudio Altmann, Haifa (IL); Yaron Ephrath, Karkur (IL)

(73) Assignee: Biosense Webster, Inc., Diamond Bar, CA (US)

( * ) Notice: Subject to any disclaimer, the term of this patent is extended or adjusted under 35 U.S.C. 154(b) by 195 days.

(21) Appl. No.: 11/424,105

(22) Filed: Jun. 14, 2006

(65) Prior Publication Data

US 2006/0241401 A1 Oct. 26, 2006

Related U.S. Application Data

(63) Continuation-in-part of application No. 11/030,934, filed on Jan. 7, 2005.

(51) Int. Cl.
*A61B 5/05* (2006.01)
*A61B 19/00* (2006.01)
(52) U.S. Cl. .................. 600/424; 600/547; 128/898; 128/899
(58) Field of Classification Search ................ 600/424, 600/547; 128/899, 898
See application file for complete search history.

(56) References Cited

U.S. PATENT DOCUMENTS

| | | | |
|---|---|---|---|
| 5,697,377 A * | 12/1997 | Wittkampf | 600/374 |
| 5,899,860 A * | 5/1999 | Pfeiffer et al. | 600/424 |
| 5,944,022 A | 8/1999 | Nardella et al. | |
| 5,983,126 A | 11/1999 | Wittkampf | |
| 6,050,267 A | 4/2000 | Nardella et al. | |
| 6,095,150 A | 8/2000 | Panescu et al. | |
| 6,161,032 A | 12/2000 | Acker | |
| 6,298,261 B1 * | 10/2001 | Rex | 600/424 |
| 6,456,864 B1 | 9/2002 | Swanson et al. | |
| 6,546,270 B1 * | 4/2003 | Goldin et al. | 600/374 |

(Continued)

FOREIGN PATENT DOCUMENTS

DE 2432173 A1 1/1976

(Continued)

OTHER PUBLICATIONS

U.S. Appl. No. 11/030,934—pending, Biosense Webster, Inc.

(Continued)

*Primary Examiner*—Max Hidenburg
*Assistant Examiner*—Sean P Dougherty
(74) *Attorney, Agent, or Firm*—Louis J. Capezzuto

(57) ABSTRACT

A method for position sensing includes placing at a known position within a body of a subject a reference probe including at least one reference electrode. Electrical currents are passed through the body between the reference electrode and body surface electrodes. Characteristics of the electrical currents are measured and are used to generate an approximation of the known position of the reference probe. A correction factor is determined based on a relationship between the approximation and the known position. A target probe including at least one target electrode is placed within the body of the subject and second electrical currents are passed through the body between the target electrode and the body surface electrodes. Characteristics of the second electrical currents are measured and used to generate a calculated position of the target probe. The correction factor is applied to correct the calculated position.

23 Claims, 2 Drawing Sheets

U.S. PATENT DOCUMENTS

| | | | |
|---|---|---|---|
| 7,536,218 B2 * | 5/2009 | Govari et al. | 600/424 |
| 2005/0288586 A1 * | 12/2005 | Ferek-Petric | 600/443 |
| 2006/0173251 A1 | 8/2006 | Govari et al. | |

FOREIGN PATENT DOCUMENTS

| | | | |
|---|---|---|---|
| EP | 0775466 A | 5/1997 | |
| EP | 1743575 A | 1/2007 | |
| WO | WO 98/48722 A | 11/1998 | |

OTHER PUBLICATIONS

U.S. Appl. No. 11/177,861—pending, Biosense Webster, Inc.
European Search Report No. EP 07 25 2388 dated Jan. 8, 2008.

* cited by examiner

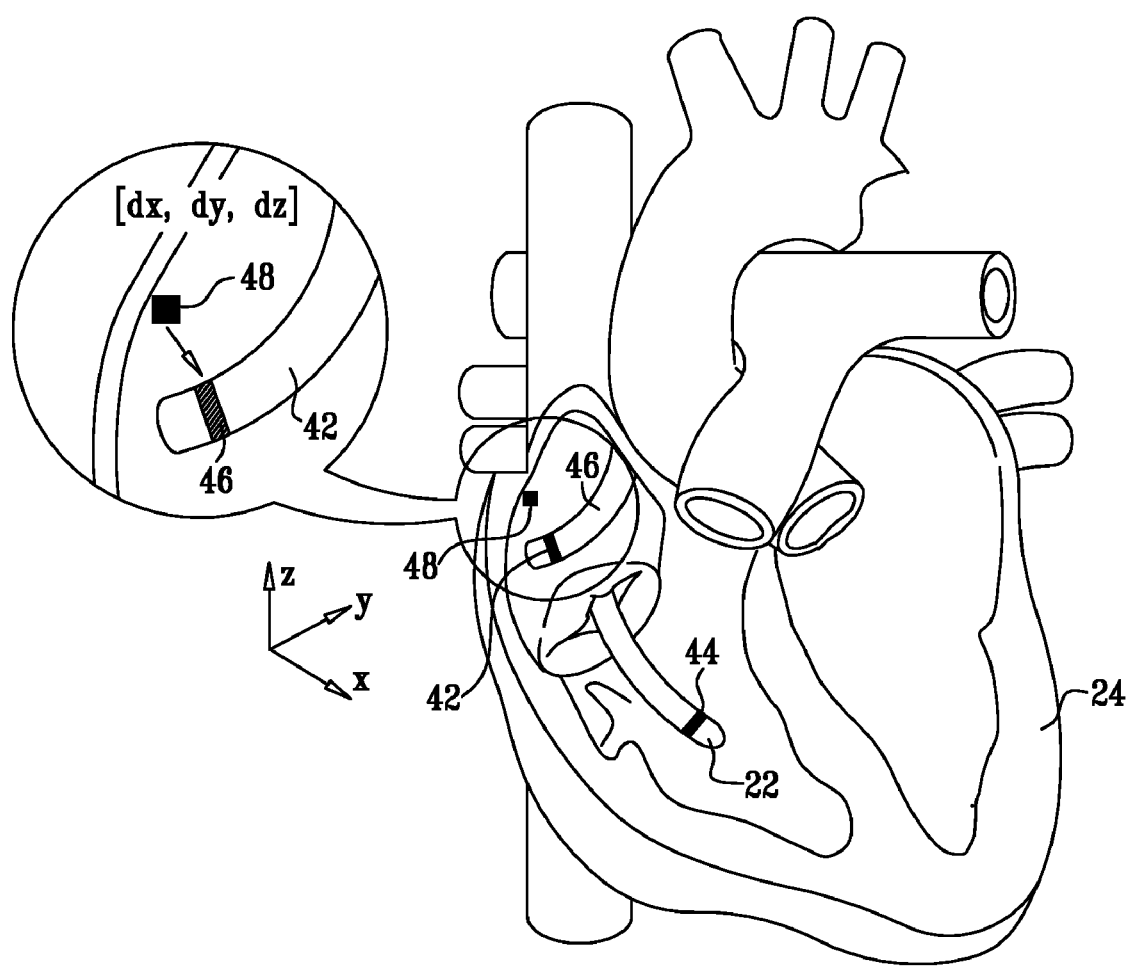

REFERENCE CATHETER FOR IMPEDANCE CALIBRATION

CROSS-REFERENCE TO RELATED APPLICATIONS

This application is a continuation-in-part of U.S. patent application Ser. No. 11/030,934 filed Jan. 7, 2005, which is assigned to the assignee of the present patent application and whose disclosure is incorporated herein by reference.

FIELD OF THE INVENTION

The present invention relates generally to sensing the position of an object placed within a living body, and specifically to position sensing using impedance measurements.

BACKGROUND OF THE INVENTION

Tracking the position of intrabody objects, such as sensors, tubes, catheters, dispensing devices, and implants, is required for many medical procedures. Systems have been developed that determine the position of an intrabody object by measuring voltage differentials between electrodes on an intrabody object and on the surface of the body. The voltage differentials correspond to the impedance between the electrodes. Methods for impedance-based position sensing are disclosed, for example, in U.S. Pat. No. 5,983,126 to Wittkampf and in U.S. Pat. No. 6,456,864 to Swanson, both of whose disclosures are incorporated herein by reference.

Wittkampf also describes a method for calibrating the position sensing apparatus using two electrodes spaced from each other on a catheter by a known distance. Measuring the voltages between each of the catheter electrodes and each of three body surface electrodes x, y, and z, permits a correlation between intrabody position and voltages in the x, y and z directions.

Similar methods for sensing voltage differentials between electrodes are disclosed by U.S. Pat. No. 5,899,860 to Pfeiffer; U.S. Pat. No. 6,095,150 to Panescu; and U.S. Pat. Nos. 6,050,267 and 5,944,022 to Nardella, all of whose disclosures are incorporated herein by reference.

SUMMARY OF THE INVENTION

Embodiments of the present invention provide efficient apparatus and methods for determining in real-time the position of a target probe placed within a living body. In these embodiments, electric currents are driven between one or more electrodes on the target probe and electrodes placed on the body surface. The impedance between the target probe and each of the body surface electrodes is measured and is used to calculate an estimated position of the target probe. A reference probe is also placed within the body, at a known location, and the impedance between the reference probe and each of the body surface electrodes is also measured. The impedance measurement for the reference probe is used to generate an impedance-based position estimate, which is compared with the known location of the reference probe. The difference between the estimated position and the known location is used to determine correction factors, which are applied to the estimated position of the target probe, thereby enhancing the accuracy of the estimate.

The process of determining correction factors and applying the correction factors to the estimated position of the target probe may be performed in real-time. In an alternative embodiment, the correction factors may be determined prior to performing the target probe impedance measurements. In the alternative embodiment, a single probe may be used initially as the reference probe to determine correction factors and may subsequently be used as the target probe.

When correction is performed in real-time, measurement errors due to impedance deviations are incorporated in real-time into the correction factors. This aspect of the invention may be used, for example, to compensate for changes of impedance of the body-surface electrodes.

Such apparatus and methods are useful, inter alia, in medical procedures, such as mapping the heart or performing ablation to treat cardiac arrhythmias.

There is therefore provided, in accordance with an embodiment of the present invention, a method for position sensing, including:

placing at a known position within a body of a subject a reference probe including at least one reference electrode;

passing electrical currents through the body between the reference electrode and a plurality of body surface electrodes while the reference probe is in the known position and measuring first characteristics of the electrical currents;

using the first characteristics to generate an approximation of the known position of the reference probe;

determining a correction factor based on a relationship between the approximation and the known position;

placing a target probe including at least one target electrode within the body of the subject;

passing electrical currents through the body between the target electrode and the plurality of body surface electrodes and measuring respective second characteristics of the electrical currents;

using the second characteristics to generate a calculated position of the target probe; and applying the correction factor to correct the calculated position.

In typical embodiments, measuring the first characteristics includes measuring an impedance between the reference electrode and the plurality of body surface electrodes, and measuring the second characteristics includes measuring an impedance between the target electrode and the plurality of body surface electrodes.

Generating the calculated position of the target probe typically includes generating coordinates of position and orientation.

The relationship between the approximation and the known position may be a difference between the approximation and the known position. The relationship may also include a ratio of the approximation and the known position.

In some embodiments, the target electrode includes multiple target electrodes, and passing the electrical currents between the target electrode and the plurality of body surface electrodes includes passing each of the electrical currents between the multiple target electrodes and one of the plurality of body surface electrodes.

Also in some embodiments, the reference electrode includes multiple reference electrodes, and passing the electrical currents between the reference electrode and the plurality of body surface electrodes includes passing each of the electrical currents between the multiple reference electrodes and one of the plurality of body surface electrodes.

Determining the correction factor may include periodically repeating a measurement of the first characteristics and updating the correction factor responsively to the repeated measurement.

In some embodiments, placing the target probe may include performing a medical procedure using the target probe. In such embodiments, the target probe may be a catheter, and performing the medical procedure may include mapping a heart of the subject. Additionally or alternatively, performing the medical procedure may include performing a therapeutic procedure.

There is further provided a method for position sensing, including:

placing at a known position within a body of a subject a probe including at least one electrode;

passing first electrical currents through the body between the at least one electrode and a plurality of body surface electrodes while the probe is in the known position;

measuring respective first characteristics of the first electrical currents;

using the first characteristics to generate an approximation of the known position;

determining a correction factor based on a relationship between the approximation and the known position;

moving the probe from the known position to a new position;

passing second electrical currents through the body between the at least one electrode and the plurality of body surface electrodes while the probe is in the new position;

measuring respective second characteristics of the second electrical currents;

using the characteristics of the second electrical currents to generate a calculated position of the probe; and applying the correction factor to correct the calculated position of the probe.

Typically, measuring the first characteristics includes measuring a first impedance between the electrode and the plurality of body surface electrodes, and measuring the second characteristics includes measuring a second impedance between the electrode and the plurality of body surface electrodes.

There is further provided apparatus for position sensing, including:

a reference probe that includes at least one reference electrode and which is adapted to be placed at a known position within a body of a subject;

a target probe that includes at least one target electrode and which is adapted to be placed within the body of the subject; and a control unit, which is operative to pass first electrical currents through the body between the at least one reference electrode and a plurality of body surface electrodes while the reference probe is in the known position, to measure first characteristics of the first electrical currents, to use the first characteristics to generate an approximation of the known position, and to determine a correction factor based on a relationship between the approximation and the known position, and which is further operative to pass second electrical currents through the body between the at least one target electrode and the plurality of body surface electrodes, to measure respective second characteristics of the second electrical currents, to use the second characteristics to generate a calculated position of the target probe, and to apply the correction factor to correct the calculated position.

Typically, the control unit is adapted to measure a first impedance between the reference electrode and the plurality of body surface electrodes, and to measure a second impedance between the at least one target electrode and the plurality of body surface electrodes.

In some embodiments, the control unit is adapted to generate coordinates of position and orientation.

The target electrode may include multiple electrodes, and the control unit may be adapted to pass each of the second electrical currents between one of the multiple electrodes and one of the plurality of body surface electrodes.

The reference electrode may include multiple electrodes, and the control unit is adapted to pass each of the first electrical currents between one of the multiple electrodes and one of the plurality of body surface electrodes.

In some embodiments, the control unit is adapted to determine the correction factor periodically and to use the correction factor to periodically correct the calculated position of the target probe.

There is further provided apparatus for position sensing, including:

a probe that includes at least one electrode and which is adapted to be placed within a body of a subject; and a control unit, which is operative to pass first electrical currents through the body between the at least one electrode and a plurality of body surface electrodes while the probe is in a known position, to measure first characteristics of the first electrical currents, to use the first characteristics to generate an approximation of the known position, and to determine a correction factor based on a relationship between the approximation and the known position, and which is further operative to pass second electrical currents through the body between the at least one electrode and the plurality of body surface electrodes while the probe is in an unknown position, to measure respective second characteristics of the second electrical currents, to use the second characteristics to generate a calculated position of the probe, and to apply the correction factor to correct the calculated position.

Typically, the control unit is adapted to measure the first characteristics by measuring a first impedance between the at least one electrode and the plurality of body surface electrodes while the probe is in the known position, and to measure the second characteristics by measuring a second impedance between the at least one electrode and the plurality of body surface electrodes while the probe is in an unknown position.

The present invention will be more fully understood from the following detailed description of the embodiments thereof, taken together with the drawings in which:

BRIEF DESCRIPTION OF THE DRAWINGS

FIG. 2 is a schematic detail view illustrating the determination of correction factors based on the distance between calculated coordinates of a reference probe and actual coordinates, in accordance with an embodiment of the present invention.

DETAILED DESCRIPTION OF EMBODIMENTS

Figure 1:
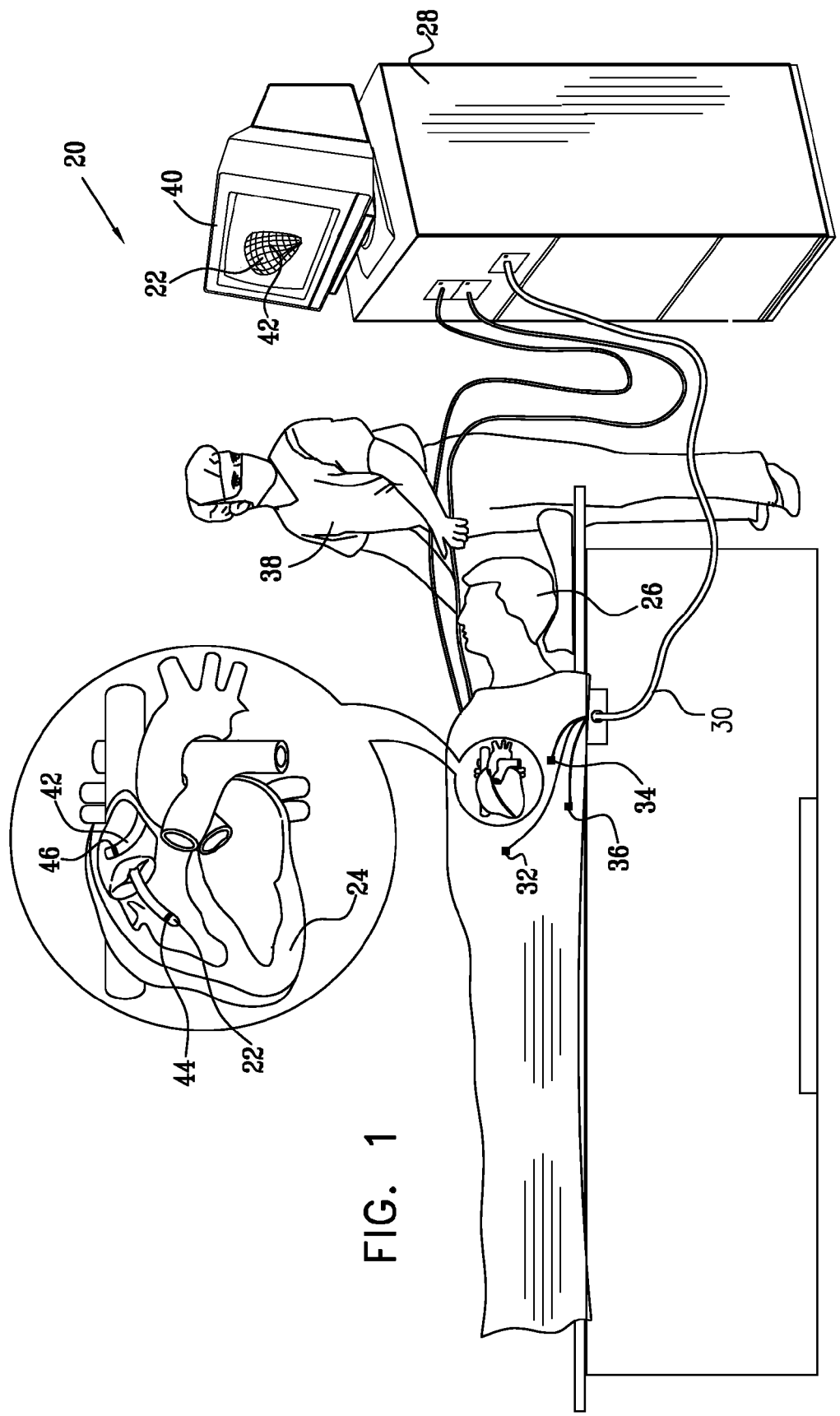
FIG. 1 is a schematic, pictorial illustration of a position sensing system used in cardiac catheterization, in accordance with an embodiment of the present invention.

FIG. 1 is an illustration of a position sensing system 20, in accordance with an embodiment of the present invention. System 20 is used in determining the position of a target probe, such as a target catheter 22, which is inserted into an internal body cavity, such as a chamber of a heart 24 of a subject 26. Typically, the target catheter is used for diagnostic or therapeutic treatment, such as mapping electrical potentials in the heart or performing ablation of heart tissue. Target catheter 22 or other target intrabody device may alternatively be used for other purposes, by itself or in conjunction with other treatment devices. (The term "target" is used in the present patent application and in the claims to denote a probe or other device whose position is to be determined by a position sensing system. The term "target" is used solely for the sake of convenience and clarity, in order to distinguish the target probe from a reference probe, and should not be construed as limiting in any way the form or function of elements to which the term is applied.)

The distal tip of target catheter 22 comprises at least one target electrode 44. Target electrode 44 is connected by wires through the insertion tube of target catheter 22 to driver circuitry in a control unit 28. Target electrode 44 may be of any suitable shape and size to implement a position sensing function described hereinbelow, and may be used for other purposes, as well, such as for electrophysiological sensing or ablation. Impedance-based position sensing is typically performed using a catheter with three electrodes, but fewer or more electrodes may also be used, as in the example provided herein.

A reference probe 42, which may be essentially identical to target catheter 22, is also inserted into the body of subject 26 and positioned at a known reference location. By way of example, for cardiac procedures, the reference location may be in the coronary sinus, or any other known location in the region of the chest cavity. The coronary sinus is a convenient choice, because invasive cardiologists are generally capable of introducing a catheter into the coronary sinus with relative ease and high reliability. Optionally, the coordinates of the reference location may be determined using a pre-acquired or real-time image, such as a MRI, x-ray, or ultrasound image.

Reference probe 42 comprises at least one reference electrode 46. Like target electrode 44, electrode 46 is connected by wires to driver circuitry in control unit 28. Similarly, electrode 44 may be of any suitable shape and size, and may be used for other purposes, as well.

The control unit is connected by wires through a cable 30 to body surface electrodes, which typically comprise adhesive skin patches 32, 34, and 36. In alternative embodiments of the invention, the electrodes on the body surface may vary in number and may take other forms, such as subcutaneous probes or a handheld device operated by a medical practitioner 38.

Patches 32, 34 and 36 may be placed at any convenient locations on the body surface in the vicinity of the target catheter and reference probe. For example, for cardiac applications, patches 32, 34, and 36 are placed around the chest of subject 26. There is no special requirement regarding the orientation of the patches relative to each other or to the coordinates of the body. In particular, there is no requirement that the placement of the patches be along fixed axes. Consequently, patch placement can be determined so as to interfere as little as possible with the medical procedure being performed.

Control unit 28 may also drive a display 40, which shows the positions of target catheter 22 and reference catheter 42 inside the body.

A process for calculating position coordinates based on impedance measurements is described in the aforementioned U.S. patent application Ser. No. 11/030,934. A related process is described in U.S. patent application Ser. No. 11/177, 861 filed on Jul. 8, 2005 which is also assigned to the assignee of the present patent application and whose disclosure is incorporated herein by reference. Methods described in the aforementioned patent applications or other methods for impedance-based position sensing may be applied by control unit 28 to measure the impedance between target electrode 44 and patches 32, 34 and 36 and to derive from the measured impedance a point, $P_{T1}$, representing the position of target catheter 22. The three-dimensional coordinates of $P_{T1}$, represented as $(x_{T1}, y_{T1}, z_{T1})$, are an approximation to the actual position of target electrode 44.

Impedance-based position sensing methods are also employed by control unit 28 to calculate a point representing the position of reference electrode 46. The difference between the calculated position of the reference probe and the known position is used to derive correction factors to improve the accuracy with which the position of the target probe is determined.

FIG. 2 is a schematic detail view illustrating how correction factors may be derived and used, in accordance with an embodiment of the present invention. Using the impedance-based position sensing methods described above, a point 48, referred to hereinbelow as $P_{R1}$, is calculated as the raw location of reference electrode 46. Point $P_{R1}=(x_{R1}, y_{R1}, z_{R1})$, is an uncorrected approximation for the location of reference electrode 46. A more precise location of the reference electrode, $P_{R2}$, comprising coordinates $(x_{R2}, y_{R2}, z_{R2})$, may be obtained using the imaging methods described above. Alternatively, this more precise location may be determined a priori based on anatomical considerations (for example, the known location of the coronary sinus relative to other anatomical features), without the use of imaging. It may be understood that in embodiments of the present invention, any convenient location may be used as the origin for the coordinate system. A typical coordinate origin is an external reference point, or one of patches 32, 34, and 36, or one of points $P_{R1}$ and $P_{R2}$.

A difference vector, [dx, dy, dz], representing the distance between point $P_{R1}$ and the more precise location $P_{R2}$ may obtained by subtracting from the $P_{R1}$ coordinates $(x_{R1}, y_{R1}, z_{R1})$ the respective $P_{R2}$ coordinates $(x_{R2}, y_{R2}, z_{R2})$, such that $dx=(x_{R1}-x_{R2})$, $dy=(y_{R1}-y_{R2})$, and $dz=(z_{R1}-z_{R2})$.

The factors dx, dy, and dz of the difference vector may be used as correction factors to determine with greater accuracy the position of target probe 22. Using the impedance-based position sensing methods described above, the location of target electrode 46 is calculated as being at the point $P_{T1}=(x_{T1}, y_{T1}, z_{T1})$. A more accurate determination of the target electrode position may be obtained by subtracting from $P_{T1}$ the difference vector, [dx, dy, dz], thereby giving a point $P_{T2}=(x_{T2}, y_{T2}, z_{T2})$, wherein $x_{T2}=(x_{T1}-dx)$, $y_{T2}=(y_{T1}-dy)$, and $z_{T2}=(z_{T1}-dz)$.

Correction factors may alternatively or additionally be derived from a ratio vector, rather than from the difference vector. A ratio vector, [rx, ry, rz], representing the ratio of coordinates of $P_{R1}$ to the coordinates of the more precise location $P_{R2}$ may obtained by dividing the $P_{R1}$ coordinates by the respective coordinates of $P_{R2}$, such that $rx=(x_{R1}/x_{R2})$, $ry=(y_{R1}/y_{R2})$, and $rz=(z_{R1}/z_{R2})$. The more accurate estimate, $P_{T1}$, of the target electrode position may then be obtained by dividing $P_{T1}$ by the ratio vector, [rx, ry, rz], thereby giving a point $P_{T2}=(x_{T2}, y_{T2}, z_{T2})$, wherein $x_{T2}=(x_{T1}/rx)$, $y_{T2}=(y_{T1}/ry)$, and $Z_{T2}=(z_{T1}/rz)$. Optionally, the position of the target probe may be corrected using a combination of multiplicative and additive factors.

The impedance measured between the target probe and patches 32, 34 and 36 may be affected over time by factors such as the lifting of a patch or increased moisture on the skin. Such factors may consequently introduce errors into the position measurements. For example, a patch may partially lift from the skin, thereby increasing the impedance at that patch. Compensation for such impedance changes is provided by generating and applying the correction factors on a real-time basis, whereby the reference impedance measurements are repeated periodically. Correction factors from the reference measurement may then be applied to the target measurement. Changes in the calculated value of $P_{T1}$ due to changing factors of impedance will also be reflected in changes to the calculated value of $P_{R1}$. Consequently, the derived correction factors will provide compensation for changing factors of impedance. Continual measurement of the reference impedance may also be used to detect and compensate for organ motion, due to patient breathing, for example.

In an alternative embodiment, target probe 22 also serves as reference probe 42. Target probe 22 is positioned at the known location and used to generate correction factors. Subsequently, the target probe is moved to perform the desired medical procedure, and impedance-based position measurements of the target probe are corrected using the measured correction factors. In this embodiment, a correction protocol may be established, whereby the target probe is returned to the known reference location, or to a new reference location, at regular intervals, in order to generate up-to-date correction factors. Alternatively, impedance variations may be corrected by methods such as those described in the abovementioned U.S. patent application Ser. No. 11/177,861 filed on Jul. 8, 2005.

The methods described hereinabove provide a means of determining a point location of target probe 22. In further embodiments of the present invention, additional target electrodes may be employed so as to provide a means for determining the complete three-dimensional orientation of target probe 22.

System 20 represents an embodiment of the invention as it may be used in a catheter-based procedure for diagnosis or treatment of conditions of the heart, such as arrhythmias. The system may be used in generating a map of the heart (for example, an electrical map, wherein the electrodes on the catheter are used alternately for position sensing and for measuring electrical potentials generated in the heart tissue). The catheter position may be superimposed on this map or on another image of the heart. System 20 can be used, as well, in the diagnosis or treatment of intravascular ailments, which may involve angioplasty or atherectomy. The principles of system 20 may also be applied, mutatis mutandis, in position-sensing systems for the diagnosis or treatment of other body structures, such as the brain, spine, skeletal joints, urinary bladder, gastrointestinal tract, prostrate, and uterus.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for position sensing, comprising:
   placing at a known position within a body of a subject a reference probe comprising at least one reference electrode;
   passing first electrical currents through the body between the at least one reference electrode and a plurality of body surface electrodes while the reference probe is in the known position;
   measuring first characteristics of the first electrical currents;
   using the first characteristics to generate an approximation of the known position of the reference probe;
   determining a correction factor based on a relationship between the approximation and the known position;
   placing a target probe comprising at least one target electrode within the body of the subject;
   passing second electrical currents through the body between the at least one target electrode and the plurality of body surface electrodes;
   measuring respective second characteristics of the second electrical currents;
   using the second characteristics to generate a calculated position of the target probe; and
   applying the correction factor to correct the calculated position.

2. The method according to claim 1, wherein measuring the first characteristics comprises measuring a first impedance between the at least one reference electrode and the plurality of body surface electrodes, and wherein measuring the second characteristics comprises measuring a second impedance between the at least one target electrode and the plurality of body surface electrodes.

3. The method according to claim 1, wherein generating the calculated position of the target probe comprises generating coordinates of position and orientation.

4. The method according to claim 1, wherein the relationship comprises a difference between the approximation and the known position.

5. The method according to claim 1, wherein the relationship comprises a ratio of the approximation and the known position.

6. The method according to claim 1, wherein the at least one target electrode comprises multiple target electrodes, and wherein passing the second electrical currents comprises passing each of the second electrical currents between one of the multiple target electrodes and one of the plurality of body surface electrodes.

7. The method according to claim 1, wherein the at least one reference electrode comprises multiple reference electrodes, and wherein passing the first electrical currents comprises passing each of the first electrical currents between one of the multiple reference electrodes and one of the plurality of body surface electrodes.

8. The method according to claim 1, wherein determining the correction factor comprises periodically repeating a measurement of the first characteristics and updating the correction factor responsively to the repeated measurement.

9. The method according to claim 1, wherein placing the target probe comprises performing a medical procedure using the target probe.

10. The method according to claim 9, wherein the target probe comprises a catheter, and wherein performing the medical procedure comprises mapping a heart of the subject.

11. The method according to claim 9, wherein performing the medical procedure comprises performing a therapeutic procedure.

12. A method for position sensing, comprising:
   placing at a known position within a body of a subject a probe comprising at least one electrode;
   passing first electrical currents through the body between the at least one electrode and a plurality of body surface electrodes while the probe is in the known position;
   measuring respective first characteristics of the first electrical currents;
   using the first characteristics to generate an approximation of the known position;
   determining a correction factor based on a relationship between the approximation and the known position;
   moving the probe from the known position to a new position; passing second electrical currents through the body between the at least one electrode and the plurality of body surface electrodes while the probe is in the new position;

measuring respective second characteristics of the second electrical currents;

using the second characteristics to generate a calculated position of the probe; and applying the correction factor to correct the calculated position of the probe.

13. The method according to claim 12, wherein measuring the first characteristics comprises measuring a first impedance between the at least one electrode and the plurality of body surface electrodes, and wherein measuring the second characteristics comprises measuring a second impedance between the at least one electrode and the plurality of body surface electrodes.

14. Apparatus for position sensing, comprising:

a reference probe that comprises at least one reference electrode and which is adapted to be placed at a known position within a body of a subject;

a target probe that comprises at least one target electrode and which is adapted to be placed within the body of the subject; and a control unit, which is operative to pass first electrical currents through the body between the at least one reference electrode and a plurality of body surface electrodes while the reference probe is in the known position, to measure first characteristics of the first electrical currents, to use the first characteristics to generate an approximation of the known position, and to determine a correction factor based on a relationship between the approximation and the known position, and which is further operative to pass second electrical currents through the body between the at least one target electrode and the plurality of body surface electrodes, to measure respective second characteristics of the second electrical currents, to use the second characteristics to generate a calculated position of the target probe, and to apply the correction factor to correct the calculated position.

15. The apparatus according to claim 14, wherein the control unit is adapted to measure the first characteristics by measuring a first impedance between the at least one reference electrode and the plurality of body surface electrodes, and to measure the second characteristics by measuring a second impedance between the at least one target electrode and the plurality of body surface electrodes.

16. The apparatus according to claim 14, wherein the control unit is adapted to generate the calculated position of the target probe by generating coordinates of position and orientation.

17. The apparatus according to claim 14, wherein the relationship comprises a difference between the approximation and the known position.

18. The apparatus according to claim 14, wherein the relationship comprises a ratio of the approximation and the known position.

19. The apparatus according to claim 14, wherein the at least one target electrode comprises multiple electrodes, and wherein the control unit is adapted to pass the second electrical currents by passing each of the second electrical currents between one of the multiple electrodes and one of the plurality of body surface electrodes.

20. The apparatus according to claim 14, wherein the at least one reference electrode comprises multiple electrodes, and wherein the control unit is adapted to pass the first electrical currents by passing each of the first electrical currents between one of the multiple electrodes and one of the plurality of body surface electrodes.

21. The apparatus according to claim 14, wherein the control unit is adapted to determine the correction factor periodically and to use the correction factor to periodically correct the calculated position of the target probe.

22. Apparatus for position sensing, comprising:

a probe that comprises at least one electrode and which is adapted to be placed within a body of a subject; and a control unit, which is operative to pass first electrical currents through the body between the at least one electrode and a plurality of body surface electrodes while the probe is in a known position, to measure first characteristics of the first electrical currents, to use the first characteristics to generate an approximation of the known position, and to determine a correction factor based on a relationship between the approximation and the known position, and which is further operative to pass second electrical currents through the body between the at least one electrode and the plurality of body surface electrodes while the probe is in an unknown position, to measure respective second characteristics of the second electrical currents, to use the second characteristics to generate a calculated position of the probe, and to apply the correction factor to correct the calculated position.

23. The apparatus according to claim 22, wherein the control unit is adapted to measure the first characteristics by measuring a first impedance between the at least one electrode and the plurality of body surface electrodes while the probe is in the known position, and to measure the second characteristics by measuring a second impedance between the at least one electrode and the plurality of body surface electrodes while the probe is in an unknown position.

\* \* \* \* \*